Figure 1:
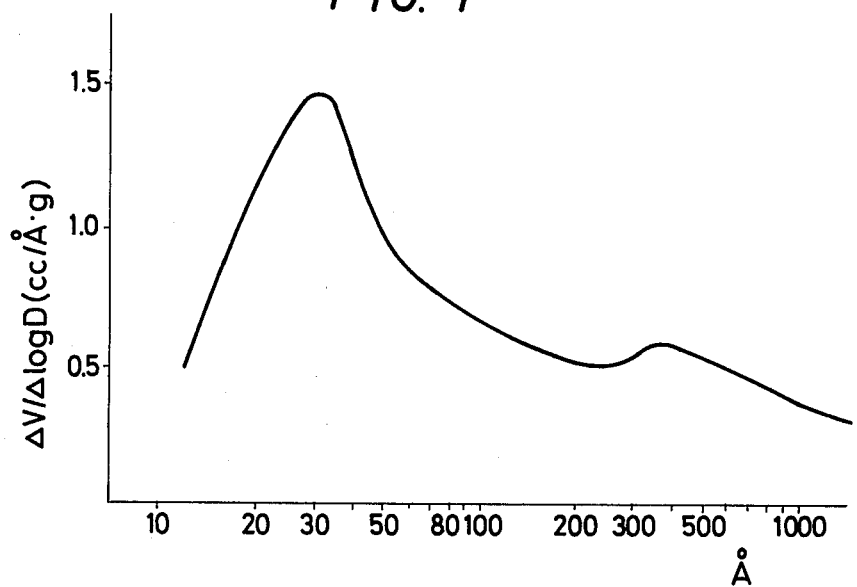

United States Patent [19]

Hidaka et al.

[11] 4,294,623

[45] Oct. 13, 1981

[54] METHOD OF PRODUCING HIGH PURITY MALTOSE

[75] Inventors: Hidemasa Hidaka, Urawa; Toshiaki Kohno, Yokohama; Toshiaki Eida, Chigasaki, all of Japan

[73] Assignee: Meiji Seika Kaisha, Ltd., Tokyo, Japan

[21] Appl. No.: 100,435

[22] Filed: Dec. 5, 1979

[30] Foreign Application Priority Data

Dec. 7, 1978 [JP] Japan ............................. 53-150547

[51] Int. Cl.³ .................... C13D 3/12; C13K 7/00; C12P 19/22
[52] U.S. Cl. .................................... 127/55; 435/95
[58] Field of Search ............... 435/95, 98, 96; 127/55

[56] References Cited

U.S. PATENT DOCUMENTS

| | | | |
|---|---|---|---|
| 3,795,584 | 5/1974 | Mitsuhashi et al. | 435/95 |
| 3,804,715 | 4/1974 | Sugimoto et al. | 435/95 |
| 3,998,696 | 12/1976 | Yomoto et al. | 435/95 |
| 4,182,634 | 1/1980 | Yamada et al. | 127/55 |

FOREIGN PATENT DOCUMENTS 52-7487  1/1977  Japan ................................. 435/95

*Primary Examiner*—Lionel M. Shapiro
*Attorney, Agent, or Firm*—Browdy and Neimark

[57] ABSTRACT

The present invention is a method of producing maltose of high purity from starch, in which starch is saccharified by β-amylase and α-amylase and/or α-1, 6-glucosidase thereby making saccharified liquor containing less than 0.5% of glucose, 60~85% of maltose, less than 5% of maltotriose together with by-products such as oligosaccharide and dextrin. And then this liquor is passed through the columns filled with granular active carbons, which have a peak of micropore diameter distribution of above and below 25 A respectively, under the condition of Special velocity (SV) below 2 thereby removing dextrin and oligosaccharide and thus producing maltose of high purity.

3 Claims, 4 Drawing Figures

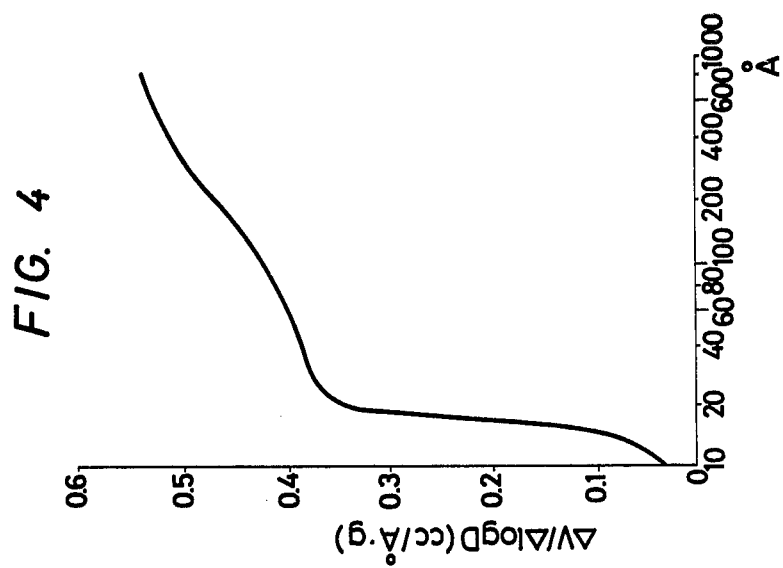
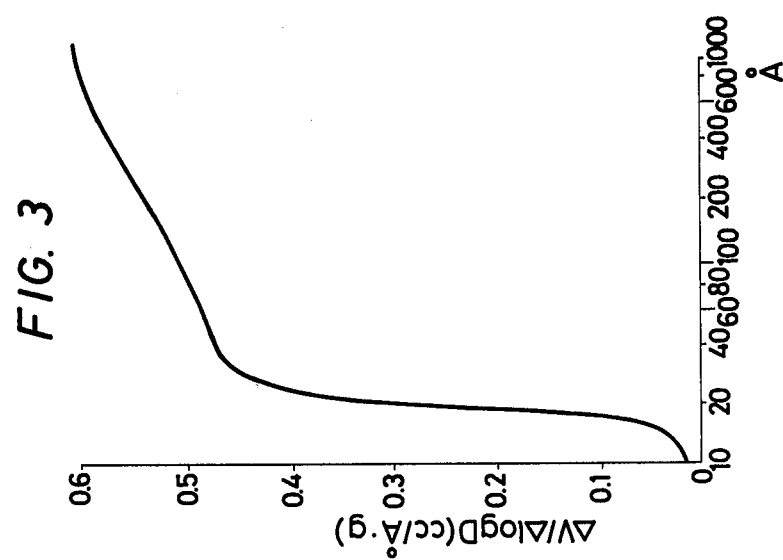

METHOD OF PRODUCING HIGH PURITY MALTOSE

The present invention relates to a method of producing maltose of high purity without the use of organic solvent, which comprises the steps of causing starch to react with β-amylase and α-amylase and/or α-1, 6-glucosidase under a limited specific condition thereby producing saccharified liquor containing less than 0.5% of glucose, 60~85% of maltose, less than 5% of maltotriose together with by-products such as oligosaccharide and dextrin, and thereafter passing said liquor through a column which is appropriately prepared by combining granular activated carbons having various micropore diameter distributions so as to remove oligosaccharide and dextrin selectively.

Maltose has been known as a main component of acid converted starch syrups and malt converted syrups because of its elegant and good sweetness. Recently people have come to prefer mild sweetness and the somewhat unfavorable effects of sucrose have been pointed out, and therefore the development of a sugar substitute which has similar physical properties to sucrose has been sought. On the other hand, recently maltose has been found to have various useful properties for food processing and also to have sweetness as low as about one third of that of sucrose. Moreover, high purity maltose is useful in the application to medicine. From these reasons, maltose is now considered as one of the most useful raw materials which has many applications for various fields, and at the same time an advantageous industrial production method has been sought.

According to the prior art, to produce high purity maltose there have been known two methods:
(1) Starch is treated with β-amylase and α-1, 6-glucosidase to directly produce high purity maltose having a maltose content of 90~95%.
(2) Starch is treated mainly with β-amylase to produce maltose and dextrin and then refined to obtain high purity maltose.

By the method (1) maltose is the main component. At the same time small qualities of maltotriose and dextrin are produced inevitably, so the purity of maltose crystals will be decreased due to the incorporation of maltotriose and dextrin in the crystals. Moreover, the purity of maltose in the mother liquor after crystalization will be decreased and it becomes most difficult to get crystals of high purity maltose from it.

On the other hand, relating to the method (2) the following methods are known: (a) Precipitation method using organic solvent (Japanese Patent Application Laying-Open No. 102854/1974), (b) Ion-exchange resin method (Japanese Patent Publication No. 46290/1977), and (c) Ultrafiltration or reverse osmosis method (Japanese Patent Application Laying-Open Nos. 98346/1976, 101141/1976, and 57344/1977). From the difficulty of removing maltotriose by these methods, it is necessary to restrain the degree of starch liquifaction to a very low level and to use only β-amylase in saccharification in order to restrict the production of maltotriose. And by the methods (a) and (c), it is very difficult to remove dextrin completely.

Meanwhile there has been known the method of refining saccharides by means of activated carbon. But this method is for preparation in a small scale. In this method all saccharides are once adsorbed on an activated carbon column. Then pass through graduately the increasing concentration of organic solvent such as lower alcohols and the saccharides are successively eluted and collected. This method is generally used in small scale preparation. But it is very hard to apply for industrial production from the following reasons: (1) hard to handle because of using powdered active carbon, (2) low adsorption quantity leads to low yield, and (3) elution with organic solvent increases the production cost.

The present inventors have tried to overcome said draw-backs in the maltose production and have made studies for development of a method of producing high purity maltose from the other viewpoint. As a result of these studies it has been found that dextrin is notably different from oligosaccharide in its adsorption behavior to activated carbon. This phenomenon depends on the micropore diameter distributions of the granular activated carbons which have heretofore been disregarded as an industrial method. And at last the present invention we accomplished by use of said phenomenon.

The characteristics of the present invention are as follows:

1. It applies the fact that (1) the higher the polymerization degree of saccharide is, the higher the affinty to the activated carbon will be, and (2) the adsorption tendency and the adsorption capacity of dextrin and oligosaccharide vary depending on the size of micropore of activated carbons.
2. The saccharified liquor is passed, through the granular activated carbon column, more than the adsorption capacity of the column. Then oligosaccharide and dextrin which have larger molecular weight than maltose are selectively adsorbed. So the fractionate of maltose are obtained by washing out the column with water.
3. Maltose obtained by the present invention has no other impurity because of no use of organic solvent or inorganic ion, so it can be brought into use directly.

Figure 2:
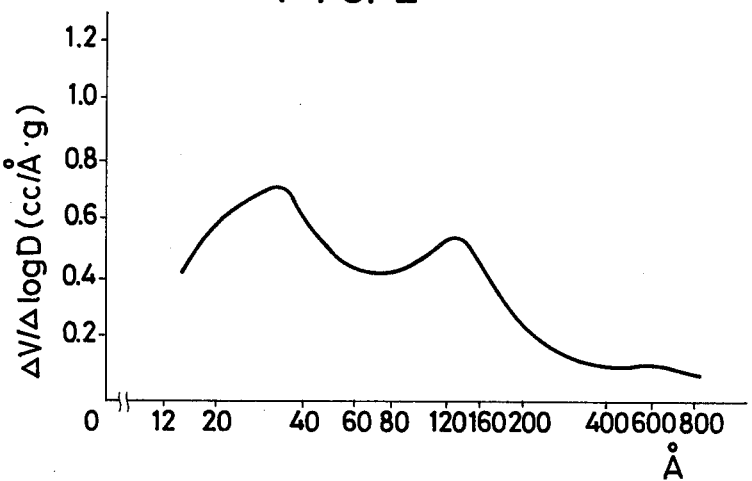

The adsorption capacity and adsorption tendency of various granular activated carbons are summarized in table-1. Dextrin refers to a saccharide which preciptates in 50% acetone solution, and oligosaccharide refers to a saccharide which does not precipitate in 50% acetone solution. In FIGS. 1~4 micropore diameter distribution of various granular activated carbons are shown.

FIGS. 1~4 are diagrams showing micropore distribution of various granular activated carbons, wherein, in relation to Table 1, FIGS. 1, 2, 3 and 4 show carbon B, D, E and F, respectively.

TABLE 1

Adsorption capacity and adsorption tendency of various granular activated carbons

| | Main peak of micropore diameter distribution (Å, BET method) | Adsorption capacity (g/g carbon) | | Adsorption tendency a/b |
|---|---|---|---|---|
| | | a oligosaccharide | b dextrin | |
| Carbon A | 30–40 | 0.05 | 0.15 | 0.33 |
| Carbon B | 30 | 0.15 | 0.39 | 0.38 |
| Carbon C | 30 | 0.15 | 0.40 | 0.38 |
| Carbon D | 30 | 0.29 | 0.34 | 0.85 |
| Carbon E | 20 | 0.32 | 0.21 | 1.52 |
| Carbon F | 15 | 0.40 | 0.24 | 1.67 |
| Carbon G | 10 | 0.29 | 0.06 | 4.83 |

TABLE 1-continued

Adsorption capacity and adsorption tendency of various granular activated carbons

| Main peak of micropore diameter distribution (A, BET method) | Adsorption capacity (g/g carbon) | | Adsorption tendency a/b |
|---|---|---|---|
| | a oligosaccharide | b dextrin | |
| Carbon H | 10 | 0.31 | 0.05 | 6.20 |

As shown in table 1 and FIGS. 1~4, granular activated carbons have various micropore distributions depending on raw material, pretreatment, activation method, etc. The adsorption tendency of saccharides varies depending on the micropore distribution. The main peak of the micropore diameter distribution changes adsorption tendency of dextrin and oligosaccharide between 20 and 30 Å. Granular activated carbon having larger diameter adsorbs dextrin well and one having smaller diameter does oligosaccharide well.

As described above, it has been discovered that the adsorption tendency of saccharides varies remarkably depending on the micropore diameter distribution of granular activated carbons. On the basis of this discovery the fact has been found that by passing saccharified liquor containing maltose, oligosaccharide and dextrin through an activated carbon column of a micropore diameter above 25 Å, mainly dextrin can be selectively removed and, in case of below 25 Å, mainly oligosaccharide can be selectively removed, thereby enabling the production of high purity maltose at a high yield. The present invention has been attained as a result of the study on the basis of this knowledge.

Hereinafter the present invention will be explained in detail.

In the present invention any starches such as corn starch, potato starch, sweet potato starch, and tapioca starch may be used as raw material. For the liquefaction of starches it is possible to use an enzymatic liquefaction or a mechanical liquefaction etc. It is preferable to perform the liquefaction slightly in order that oligosaccharide as well as maltotriose are not produced excessively. The liquefaction is desirable to be done below Dextrose Equivalent (DE) 10, preferably below DE 4.

At first starch is suspended in water at concentration of 10~30%, and liquefying γ-amylase is added to the suspension. Then it is heated at 80°~100° C., thereby obtaining a liquefied liquor. Subsequently, this liquefied liquor is rapidly cooled to 50°~60° C. and then added with β-amylase of 50~1000 unit/g-starch, α-amylase of 1~10 unit/g-starch and if desired, α-1, 6-glucosidase of 1~10 unit/g-starch. Then the mixture is subjected to saccharification at pH 5.0~6.5, 50°~60° C. for 4-24 hours thereby obtaining a saccharified liquor containing glucose ($G_1$) of no more than 0.5%, maltose ($G_2$) of 60~85%, maltotriose ($G_3$) of no more than 5%, and together with oligosaccharide and dextrin of 9.5~34.5%. According to the prior method, as described above, it is difficult to separate maltotriose from maltose, so that maltotriose remains and thereby the quality of maltose becomes lower and therefore it is necessary to suppress its production during saccharification process as much as possible. On the contrary, the method of the present invention using granular activated carbon is capable of removing maltotriose to some extent. So the content below 5% of maltotriose in the saccharified liquor is an allowable range and does not cause any trouble in the following steps. As described above, the saccharification process of the present invention which can be attained by the combination of β-amylase and α-amylase and/or α-1.6-glucosidase, is different from the prior method which only uses β-amylase. The present method is advantageous in following points:

(1) Higher yield of maltose in saccharification process.
(2) Need not to pay particular consideration to the retrogradation of starch.
(3) Higher concentration liquefaction and saccharification are available.

In this invention any α-amylase can be used, it is preferable however, to use streptomyces α-amylase (Japanese Patent Publication No. 1871/1974) which produces maltose in a remarkable content.

The saccharified liquor thus obtained may be subjected to decoloration and desalting by use of powdered activated carbon and ionexchange resin etc. It is also possible to previously perform ultrafiltration or reverse osmosis to partly remove dextrin and oligosaccharide.

As shown in table 1, typical granular activated carbons for separating dextrin are B, C, D and for oligosaccharide are E, F, G, H. In order to remove oligosaccharide and dextrin together with effectiveness, it is preferable to use a combination of these two kinds of granular activated carbons. The granular activated carbon is almost ineffective in the batch system. Therefore it is used in the column system and if necessary together with Celite (Johns Manville) etc. to raise separation efficiency. Also the column may be used in the pulse-bed system or the merry-go-round system to raise the efficiency.

The temperature during the adsorption treatment can be considered the as same as that of the physical adsorption. The efficiency becomes higher on the side of lower temperature, but from the points of viscosity of liquor, diffusion of dextrin and oligosaccharide inside the granular active carbon, and to raise Special velocity (SV), it is preferable to raise the temperature to some extent. In general a temperature in the range between room temperature and 90° C., preferably 50°~70° C. may be used. Also, there is almost no influence on the adsorption of pH during treatment, and therefore it may be carried out in any pH range in which the saccharide does not cause decomposition. Usually it can be done within a range of pH 3~7.

A considerably high concentration of saccharified liquor may be used, but it is preferable to use a range of 10~30% in view of treatment temperature and pressure loss of the column etc.. The applying load on the column varies depending on conditions such as saccharide composition of the saccharified liquor, sort of the using granular activated carbon, combination of said carbons, maltose content required, etc. Generally it is possible to apply a load of 0.3~5 times by dry weight as much as granular activated carbon.

SV is available below 2, preferably 0.5~1. If necessary, it is possible to perform the recycle method on column to raise the separation efficiency thereby improving the purity.

Water such as industrial water, tap water, and deionized water are available for washing out maltose in the column after passing the saccharified liquor. If saccharified liquor is decolored and desalted prior to the passing carbon column, and eluted with deionized water, it is possible to obtain a high purity maltose for food or medical use directly.

The reactivation of used carbon can be done by usual method such as kiln, alkali, acid, organic solvent, etc.

The purity of maltose liquor, obtained as described above, is no less than 97% of maltose. If desired it is also possible to obtain crystals from said liquor easily. The mother liquor removed crystals is once more passed through carbon column to raise purity. The expected high yield of maltose crystals is obtained by repeating such procedure. This is an advantage of the present invention, too.

Hereinafter the present invention will be explained in detail by examples, but the present invention is not limited to these examples.

EXAMPLE 1

1 kg of corn starch was suspended in 3.5 l of water and liquefied by bacterial α-amylase (DE 1.3). This liquor was added with β-amylase of 340 unit/g-starch and α-amylase of 9 unit/g-starch, and saccharified at 60° C., pH 6.0, for 20 hours. After deactivation of enzymes, decoloration and filtration were carried out by use of powdered activated carbon, and thereby 3 l of saccharified liquor of 25% concentration was obtained. The composition of saccharide was $G_1$ 0.1%, $G_2$ 70.9%, $G_3$ 4.3% and others 24.7%. Thereafter, this saccharified liquor was passed through a carbon column prepared by mix of 1 kg of granular activated carbon for chromatography (Wako pure chemicals) and 0.5 kg of Celite 535 (Johns Manville). The treatment was carried out at room temperature, SV=1.0. The elute was 4.0 l and 12% concentration. The composition of saccharide was $G_1$ 0.1%, $G_2$ 97.0%, $G_3$ 2.9% and dextrin was not detected. The saccharide composition was measured by gas chromatography.

EXAMPLE 2

1 kg of potato starch was suspended in 4 l of water, and liquefied by bacterial α-amylase (DE 0.7). This liquor was added with β-amylase of 340 unit/g-starch, streptomyces amylase of 1.5 unit/g-starch and α-1,6-glucosidase of 7 unit/g-starch, and saccharified at 55° C., pH 6.0 for 24 hours. After deactivation of enzyme, decoloration and desaltation mere carried out, and thereby 3 l of saccharified liquor of 20% concentration was obtained. The composition of saccharide of this liquor was $G_1$ 0.1%, $G_2$ 79.5%, $G_3$ 4.4% and others 16.0%.

The liquor was passed through carbon columns of the following composition. The first column was filled with 450 g granular activated carbon for chromatography (Wako pure chemicals), and second column was filled with 550 g of Pittsburgh granular activated carbon CAL (Pittsburgh active carbon Co.). The liquor was passed through the first column and then through the second column by descending method. The treatment was carried out at 60° C., SV=0.5. The maltose fraction of 360 g having saccharide composition of $G_1$ 0.1%, $G_2$ 98.1%, $G_3$ 1.8% was obtained. The saccharide composition was measured by gas chromatography.

What we claimed is:

1. Method of producing high purity maltose having more than 97% of maltose content from a saccharified liquor containing less than 0.5% of glucose, 60~85% of maltose and less than 5% of maltotriose, the remainder oligosaccharide and/or dextrin, comprising passing said saccharified liquor through a column filled with granular activated carbon having a peak micropore diameter above 25 Å, thereby removing mainly dextrin, and then passing the liquor through a column filled with granular activated carbon having a main peak of micropore diameter distribution below 25 Å, thereby removing mainly oligosaccharide, and eluting without using any organic solvent.

2. Method as claimed in claim 1, wherein the saccharified liquor is passed through said granular activated carbon column at 50°~70° C., SV 0.5~1.0.

3. Method as claimed in claim 1, wherein a load is used to 0.3~5 times by dry weight as much as granular activated carbon.

* * * * *